(12) United States Patent
Uhl (10) Patent No.: US 10,520,713 B2
(45) Date of Patent: Dec. 31, 2019

(54) SYSTEM FOR CONFOCAL ILLUMINATION OF A SAMPLE

(71) Applicant: Till I.D. GmbH, Graefelfing (DE)

(72) Inventor: Rainer Uhl, Munich (DE)

(73) Assignee: TILL I.D. GMBH, Planegg/Martinsried (DE)

( * ) Notice: Subject to any disclaimer, the term of this patent is extended or adjusted under 35 U.S.C. 154(b) by 479 days.

(21) Appl. No.: 15/227,069

(22) Filed: Aug. 3, 2016

(65) Prior Publication Data

US 2017/0038573 A1 Feb. 9, 2017

(30) Foreign Application Priority Data

Aug. 6, 2015 (DE) ........................ 10 2015 112 960

(51) Int. Cl.
*G02B 21/00* (2006.01)
*G02B 21/16* (2006.01)
*G01N 21/64* (2006.01)

(52) U.S. Cl.
CPC ..... *G02B 21/0032* (2013.01); *G02B 21/0044* (2013.01); *G02B 21/16* (2013.01); *G01N 21/6458* (2013.01); *G01N 2021/6478* (2013.01)

(58) Field of Classification Search
CPC ....................... G02B 21/0032; G02B 21/0044; G02B 21/16; G01N 21/6458; G01N 2021/6478

(Continued)

(56) References Cited

U.S. PATENT DOCUMENTS 5,428,475 A 6/1995 Tanaami et al.
5,479,252 A * 12/1995 Worster ............. G01N 21/9501
250/559.42

(Continued)

FOREIGN PATENT DOCUMENTS

EP 1 359 452 A1 11/2003

OTHER PUBLICATIONS

Katsumasa Fujita, Osamu Nakamura, Tomoyuki Kaneko, Masahito Oyamada, Tetsuro Takamatsu, Satoshi Kawata, Confocal Multipoint Multiphoton Excitation Microscope with Mircolens and Pinhole Arrays, Optics Cmmunications, 174 Jan. 15, 2000, pp. 7-12.

(Continued)

*Primary Examiner* — Evan P Dzierzynski
*Assistant Examiner* — Mitchell T Oestreich
(74) *Attorney, Agent, or Firm* — David S. Safran; Roberts Mlotkowski Safran Cole & Calderon, P.C.

(57) ABSTRACT

A system for confocal observation of a sample, having a mask, which is arranged in both an illumination beam path and in an image beam path and which is rotatable around a central axis, openings arranged in a pinhole plane, an arrangement of focusing micro-optics aligned with the geometric arrangement of the openings of the mask to generate a focal pattern, and an optical assembly with an objective, and which is configured to image the focal pattern onto the sample for generating an illumination pattern moving across the sample and to collect light from the sample by the objective and to image it onto the openings of the mask for confocal filtering. The focal plane and pinhole plane are separated by a distance and the optical assembly has a path length difference compensation arrangement which is selective with regard to the illumination light and the light collected from the sample.

36 Claims, 6 Drawing Sheets (58) Field of Classification Search
USPC ........................................................ 359/389
See application file for complete search history.

(56) References Cited

U.S. PATENT DOCUMENTS

| | | | |
|---|---|---|---|
| 5,717,519 A | 2/1998 | Sugiyama et al. | |
| 6,300,618 B1 | 10/2001 | Tanaami et al. | |
| 7,580,171 B2 * | 8/2009 | Uhl .................... | G02B 21/0032 359/235 |
| 7,706,043 B2 | 4/2010 | Uhl et al. | |
| 2015/0131148 A1 | 5/2015 | Redford | |

OTHER PUBLICATIONS

Alexander Egner and Stefan W. Hell, Time Multiplexing and Parallelization in Multifocal Multiphoton Microscopy, J. Opt. Soc. Am. A/vol. 17, No. 7, Jul. 2000, pp. 1192-1201.

* cited by examiner

SYSTEM FOR CONFOCAL ILLUMINATION OF A SAMPLE

BACKGROUND OF THE INVENTION

Field of the Invention

The present invention relates to a system for confocal observation of a sample.

Description of Related Art

Spinning disc systems (i.e., confocal microscope systems based on the Nipkow principle), comprising camera-based parallel detection, have become increasingly popular in live cell microscopy. The method for imaging using a plurality of light spots was first described by P. G. Nipkow in 1884 and was used subsequently, for example, in (mechanical) television technology ("Televisor"). Therein a pinhole disc is rotated around a central rotation axis, and all areas of the object to be observed are illuminated through the pinholes equally long. The rotating disc is generally called Nipkow disc. Nipkow microscope systems are fast and gentle to live cells; however, they suffer from a low light efficiency if only the small fraction of light is utilized in the excitation beam-path which passes through the pinholes without prior focusing.

In the 1990's Japanese engineers at the Yokogawa company were first to successfully utilize micro-lenses in a corresponding second disk to concentrate excitation intensity onto the pinholes of the first disk, thus increase the light throughput considerably. To this end the second disc is located in the illumination beam path in front of the pinhole disc in such a manner that the pinhole plane coincides with the focal plane of the micro-lenses and that the focal points generated by the micro-lenses fall exactly onto the pinhole openings. If now both discs rotate around a common axis, one obtains many (typically more than 1000) simultaneously illuminated spots on the sample which—by rotation—sequentially illuminate the entire area of the sample seen by the detector. The emission generated by these illuminated spots is then detected by a camera with confocal filtering through the pinholes. Examples for such methods, wherein both the excitation light and the emission light passes through the pinholes, are described in U.S. Pat. Nos. 5,428,475, 5,717,519 and 6,300,618.

There are substantial drawbacks of methods where both excitation-and emission beams have to pass through the same pinholes: They result from the combination and separation, respectively, of the excitation beam and the emission beam, which has to take place in the finite optical space between the micro-lenses disc and the pinhole disc. These inherent drawbacks can be avoided if—as described in U.S. Pat. No. 7,706,043 B2 or 7,580,171 B2—combination and separation of excitation beam path and emission beam path, respectively, are realized in a real infinite space which is located, as seen from the objective, behind the Nipkow disc. In the examples described in U.S. Pat. No. 7,706,043 B2 or 7,580,171 B2 micro-optics and pinholes are combined in a common disc, wherein the excitation light and the emission light cross the same pinholes, but in opposite direction.

For the case of excitation by multi-photon absorption A. Egner and S. W. Hell have presented in "Time multiplexing and parallelization in multi-focal multi-photon microscopy", J. Opt. Soc. Am. 17, 1192-1200, in 2000 a two-photon spinning disc system wherein spatial filtering of the emission light through confocal pinholes—due to the two-photon excitation—is not mandatory. In the same year, K. Fujita at al. (Optics Communications, vol. 174, pages 7-12) have shown that with the help of pinholes image quality may be improved.

SUMMARY OF THE INVENTION

It is an object of the present invention to provide for a confocal system for observation of a sample utilizing a rotating pinhole mask, which is light-efficient and which has nevertheless a relatively simple structure.

According to the invention, this object is achieved by a confocal system as described herein.

The solution according to the invention enables the realization of a highly light-efficient confocal system which nevertheless has a relatively simple structure. We achieve this by avoiding the need to send excitation- and emission light collected from the sample through the same pinhole. We utilize pinholes in the emission beam-path only, i.e., only the light originating from emission in the sample is confocally filtered by the pinholes, while the excitation spots are created in a space between disc and microscope. Given that the disc serves two purposes in this arrangement, namely to generate a rotating focus pattern for excitation and confocal filtering for emission, and given that lenses and their focal planes cannot lie on the same disk, one needs to compensate for the path length difference encountered by the excitation-beam compared to the emission beam. Since excitation and emission beams can be separated and united by means of their different color, one can have one travel on a path, which differs from the other one such that the path lengths are precisely matched. By incorporating a suitable "path length difference compensation arrangement" in the finite beam path of the emission beam before—as seen from the objective—it reaches the pinhole mask, one may, for example, generate an excitation spot pattern in front of a disc by a micro-lenses on this disc and—at the same time—achieve confocal spatial filtering by pinholes carried by the same disc. The path length difference compensation arrangement compensates for the beam path difference between the position of the focal plane of the micro-optics and the position of the pinhole plane for the light collected from the sample.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIGS. 7b and 7c show different alternatives of the system of FIG. 7a;

DETAILED DESCRIPTION OF THE INVENTION

In general, concerning the presentation of the beam path in the Figures it is to be taken into account that for illustrative purposes usually the focal distance of the micro-optics (micro-lenses) relative to the focal length of the macro-optics are shown much too large (for example, a typical ratio in practice would be approximately 1:30 (for example, 3 mm vs. 90 mm)).

The principle of a first embodiment is schematically shown in FIGS. 1 to 4, which, in many practical cases, might be a more convenient and more feasible alternative to light-sheet microscopy.

Figure 1:
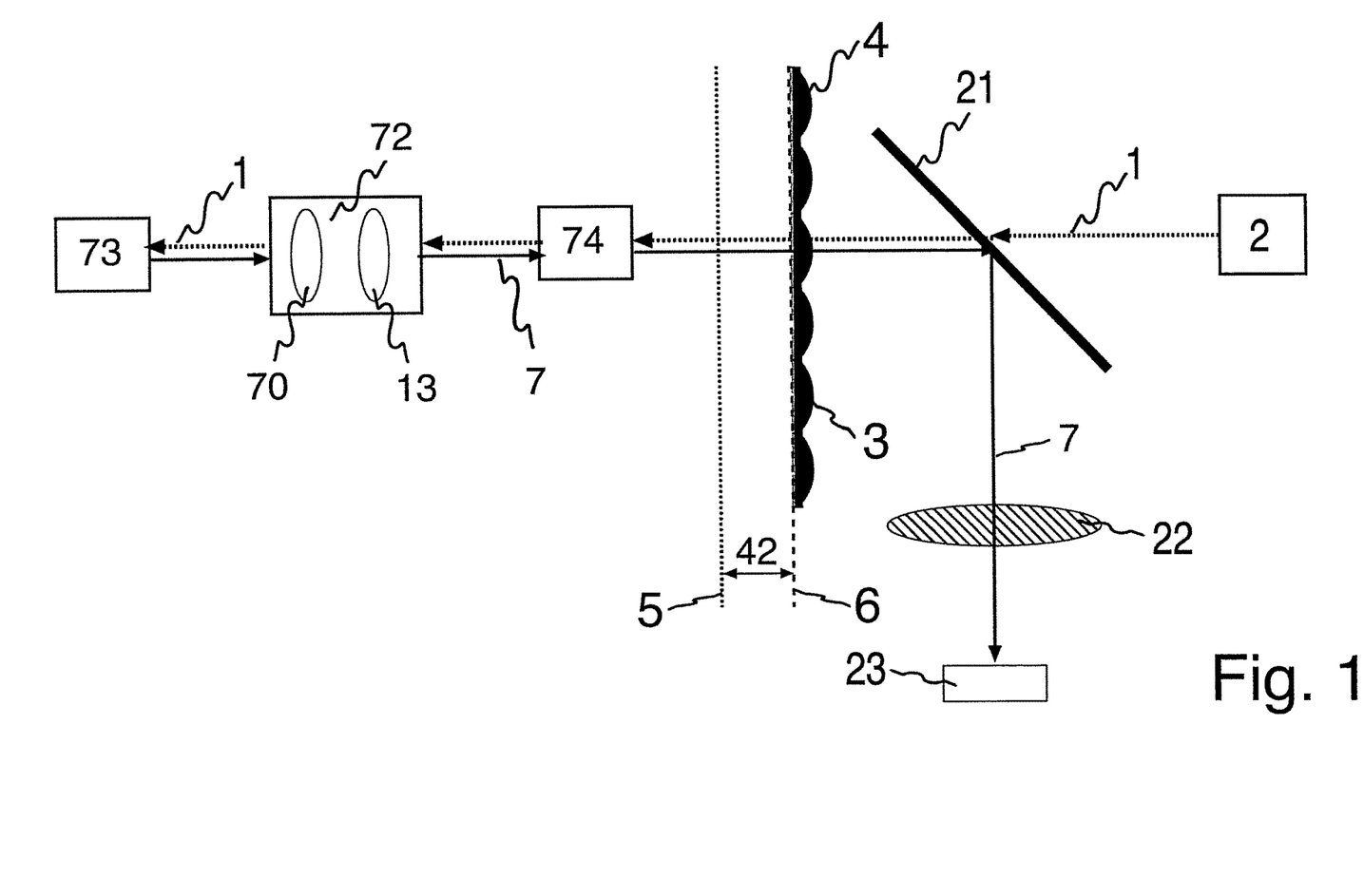
FIG. 1 is a schematic illustration of the beam path in a first example of a confocal system according to the invention.

Therein the two-dimensionally widened excitation beam (i.e., the illumination light beam) 1 of a short-pulse light source 2 suitable for generating multi-photon absorption impinges onto a rotating disc 3, which comprises a plurality of micro-lenses 4, which are arranged in the focal plane 5 of the micro-lenses 4 like a Nipkow disc for generating a suitable spot pattern. This spot pattern originates—as seen from the objective 70 in front of the disc 3 and is imaged by an optical assembly 72 consisting of a tube lens 13 and the objective 70 into the sample 73, where it generates a rotating excitation pattern resulting in a corresponding emission pattern generated by the sample 73. The image of the emission pattern would—after having passed through the objective 70 and the tubular lens 13—likewise fall within the focal plane 5, i.e., before the disc, if excitation and emission light (i.e., light collected from the sample by the optical assembly 72) took the same path.

However, if both beams are separated and subsequently recombined again, and if they are guided on different paths travelling different distances, the image plane 6 for the emission beams 7 can be made to fall exactly onto the plane of pinholes 8 of a mask, thereby achieving a confocal spatial-filtering effect whilst using a single disc 3, only. To this end, the disc 3 has to comprise a pinhole pattern corresponding to the arrangement of the micro-lenses 4. In order to avoid the requirement to "squeeze" the excitation light beam 1 through the same pinholes 8 as the emission light beam 7, the pinhole openings 8 are not surrounded by a blackened periphery but rather by a long-pass coating 9, which allows the long-wavelengths excitation light to pass and which acts for the shorter wavelengths emission light only as a pinhole (i.e., the long-pass coating 9 actually forms the mask). Each pinhole 8 is arranged on the optical axis of one of the micro-lenses 4. The mask with the pinholes 8 and the micro-lens arrangement thus jointly form the disc 3. The pinholes 8 and the micro-lens arrangement each are arranged concentrically around the central axis, with the mask, as already mentioned, being designed as a Nipkow disc.

Figure 2A:
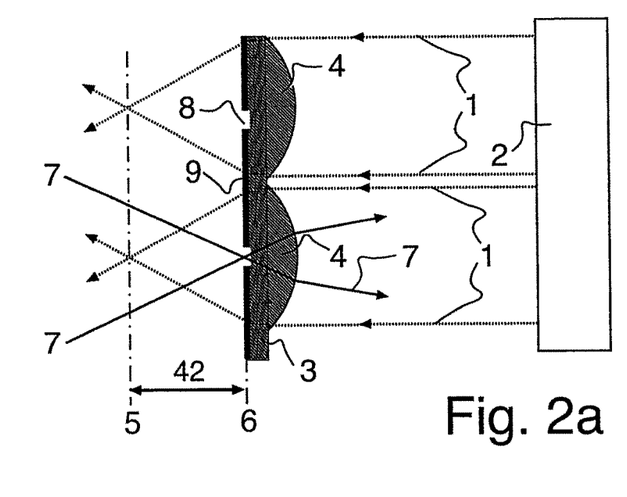
FIGS. 2a to 2d are schematic views of part of the system of FIG. 1 in the region of the Nipkow disc without the beam splitter being shown, wherein various alternatives are shown.

In the embodiment shown in FIG. 2a, wherein the micro-lenses 4 (as seen by the emission beams 7) are located behind the mask with the pinholes 8, the emission beams 7 focused through the pinholes 8 are rendered more convergent by the micro-lenses 4 (i.e., their numerical aperture is reduced), whereby an enlarged virtual image of the pinholes originates, which is then imaged onto the camera. This effect causes a slight resolution reduction, whose extent increases with increasing disc-thickness, i.e., the larger the distance between lens surface and pinhole is. If the disc is reversed in the beam path, as shown in FIG. 2d, so that the micro-lenses 4 now—as seen by the emission beams 7—are located before the mask with the pinholes 8, the micro-lenses 4 in the excitation beam 1 are not passed "lege artis", but this is not relevant, since the imaging still remains limited by diffraction. The virtual image of the pinholes in this case is scaled down, i.e., resolution is slightly increased.

Figure 2B:
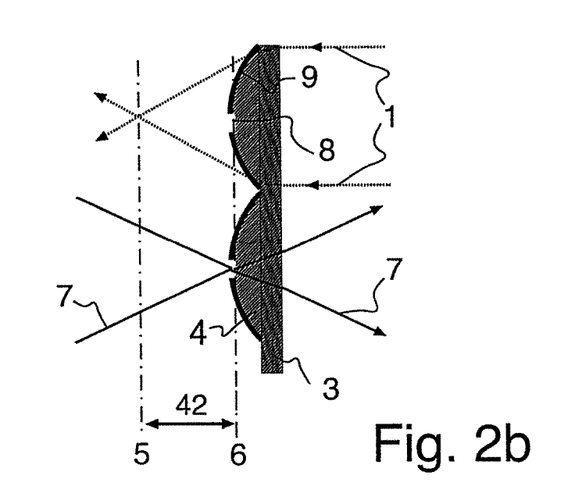
Figure 2C:
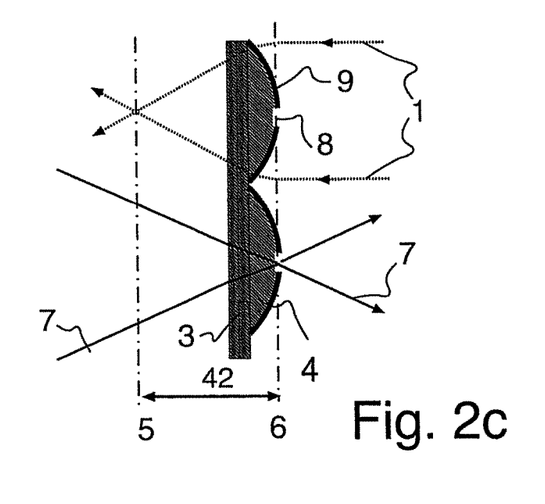
Figure 2D:
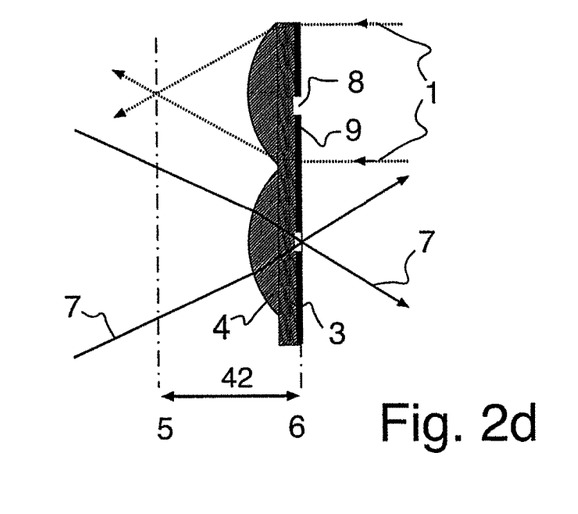

However, the two embodiments shown in FIGS. 2b and 2c have no effect on the (virtual) size of the pinholes 8, in which embodiments the micro-lens surfaces and the pinholes are arranged at the same side of the disc 3 by providing the long-pass coating 9 directly on the surface of the micro-lenses 4. In the embodiment of FIG. 2b, like in FIG. 2a, the long-pass coating 9 is provided on the side of the disc 3 facing the emission beams 9, whereas in the embodiment of FIG. 3c, like in FIG. 2d, the long-pass coating 9 is located at the side of the disc 3 facing away from the emission beams 7.

The actual choice from the embodiments shown in FIGS. 2a to 2d may, for example, depend on the question for which embodiment the manufacturing process provides for the best results.

Figure 4:
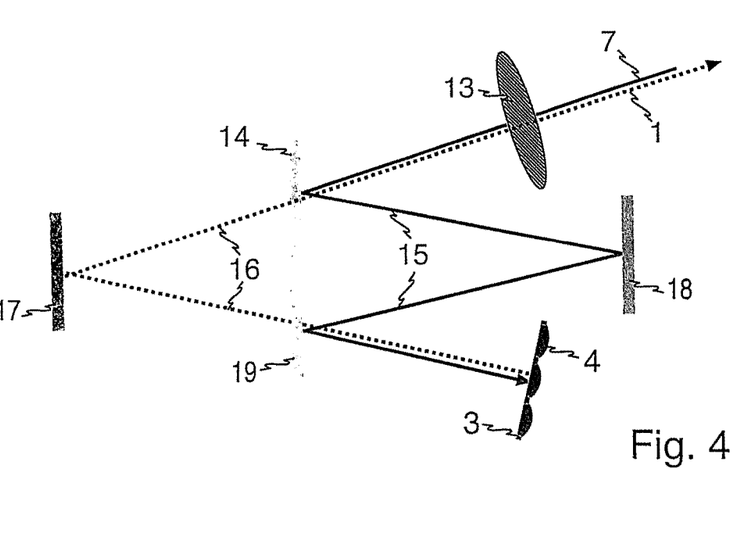
FIG. 4 is a schematic view of an example of a path length difference compensation arrangement of the system of FIG. 1.

In any case the necessary path length difference compensation between the excitation beams 1 and the emission beams 7 occurs in the finite space of the beam path, i.e., between the tube lens 13 and the disc 3, by means of a suitable path length difference compensation arrangement 74 (FIG. 4), which is configured such that the optical distance 42 between the focal plane 5 and the plane of the pinholes 8 is compensated for the emission light. In the example of FIG. 4 the beams are spectrally "separated" by means of a long-pass filter 14, they are guided along different paths 15 and 16, respectively, they are reflected by a mirror 17 and 18, respectively, and then they are "combined" again by means of a further long-pass filter 19. Since the excitation light beams and the emission light beams travel in opposite directions, this "separation" and "combination" is not to be understood literally (where such an "separation" is seen and where such a "combination" is seen depends on the direction in which one follows the two beams), but rather generally in the sense that the path length difference compensation arrangement and its dichroic beam splitter create a region in which the excitation light beams and the emission light beams are separate, i.e., they travel on different paths 15, 16.

The two long-pass filters 14, 19 of FIG. 4 could be replaced by a combination of a long-pass filter and a short-pass filter. Generally, in the path length difference compensation arrangement the first beam splitter, as seen from the objective, may be a long-pass, wherein then the second beam splitter could be a long-pass or a short-pass, or wherein the first beam splitter is a short-pass, wherein then the second beam splitter likewise could be a long-pass or a short-pass. In any case, one has to take care that the beam splitters are used with small angles of deflection and with thin substrates, since otherwise image defects may occur which impede diffraction-limited imaging.

Figure 3:
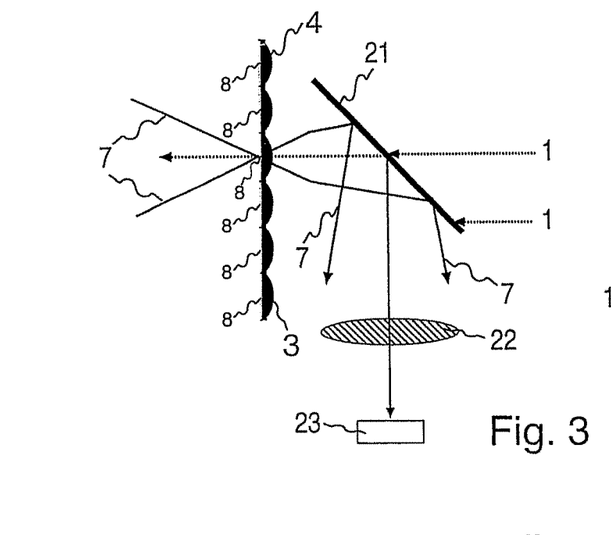
FIG. 3 is a schematic view of part of the system of FIG. 1, wherein the beam splitter and the detector are included.
Figure 5:
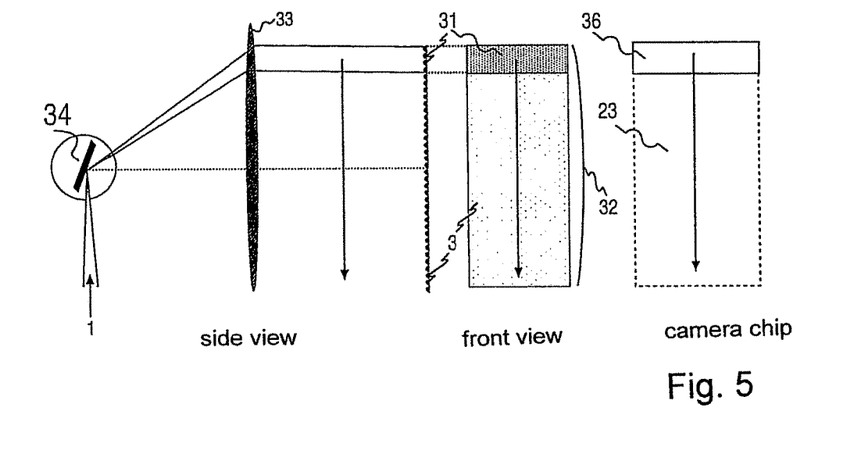
FIG. 5 is a schematic view of a system for sequential illumination and imaging of the sample to be used in the system shown in FIG. 3.
Figure 6:
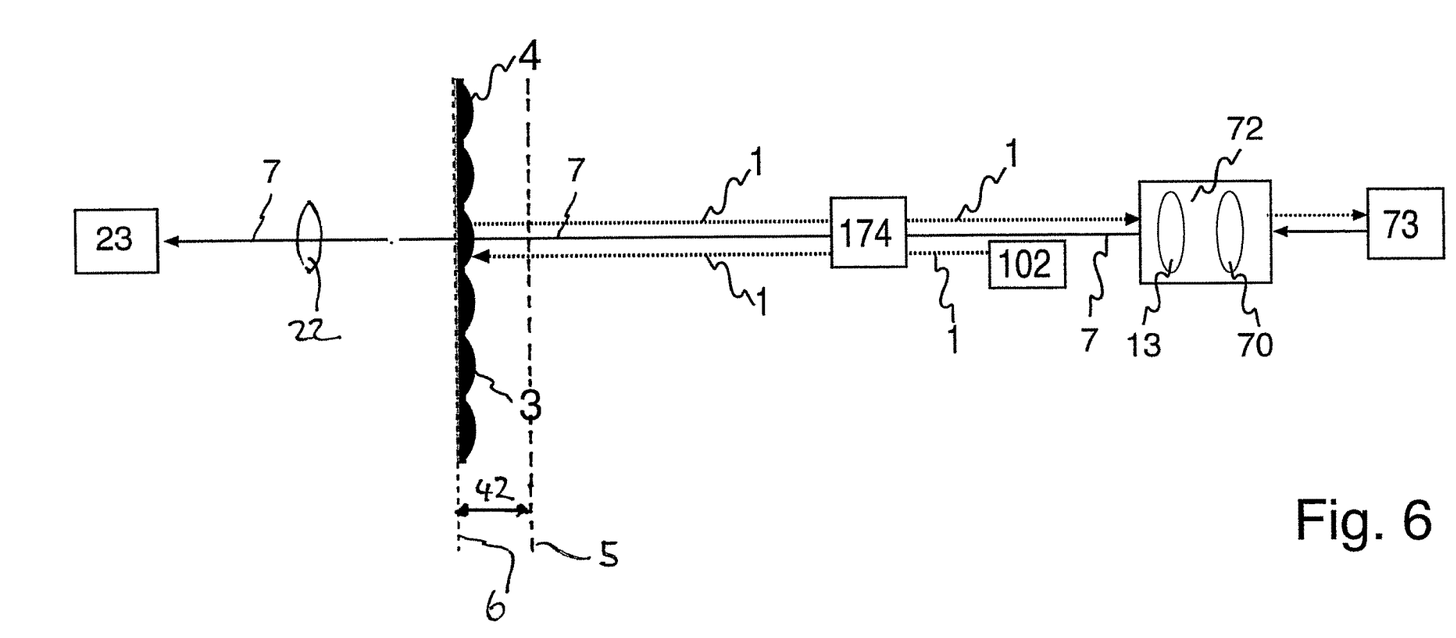
FIG. 6 is a schematic view of the beam path in a second example of a confocal system according to the invention.

The image beam path, i.e., the collected emission light 7, after having passed the pinholes 8 and the micro-lenses 4 of the disc 3, is coupled out by means of a beam splitter 21 and is projected via a suitable optics 22 onto the chip 23 of a camera acting as a detector and is recorded there. Given that in beam splitters like 21 the coatings tend to warp their substrate, transmitting the emission beam path 7 and reflecting the IR excitation light 1 is a preferred measure because beam-splitter imperfections cause less pronounced image distortions this way. Given that the available light power of IR-fs (femtoseconds, i.e., $10^{-15}$ sec.) lasers usually will not be sufficient to illuminate an entire camera field simultaneously with the desired spot pattern, only a partial field 31 will usually be illuminated as illustrated in FIG. 5. This partial field can be moved on the disc 3 in order to obtain an image 32 of the entire field, preferably by means of a suitable optics 33 and a galvanometer mirror 34, which is located at a suitable location in the beam path and which positions the excitation light 1 in the desired partial area shape on the disc 3. According to a preferred embodiment of this concept, such movement occurs continuously and in a manner such that the illuminated partial field 31 moves synchronously with regard to the respectively detected "rolling shutter" partial field 36 of a CMOS camera chip 23 (i.e., the chip 23 is red out in a manner which mimics the movement of a shutter), as is known in the art as such. In this manner the large field does not have to be composed of partial images, but rather one obtains already a complete image by a single shutter run.

The concept illustrated by reference to FIGS. 1 to 5 in general also may be employed in one-photon excitation. However, the filter coating 9 with the pinholes 8 then has to be configured as a short-pass in order to allow the excitation light to pass through (in one-photon excitation the excitation light consists of shorter wavelengths than the emission light). In case that several different excitation wavelengths are to be used, the filter coating 9 has to be configured as a corresponding multi-band coating. However, this seems to be of low feasibility.

Therefore, in FIGS. 6 to 10, a more feasible concept for a confocal system for one-photon excitation is shown. This alternative concept likewise requires only a single Nipkow disc and achieves the path length difference compensation between excitation light and emission light (by separation and subsequent combination of excitation light and emission light) in the finite space before—as seen from the objective—the disc.

However, in contrast to the previous concept, in a first embodiment of this concept (FIG. 7a) the disc 3 is two-dimensionally illuminated—as seen from the objective 70—by a collimated excitation light beam 1 from ahead. The illumination spot pattern is created by refraction at the convex micro-lenses 4 of the Nipkow disc 3, subsequent reflection at the mirror surface 40 and further focusing upon passing the convex micro-lens surfaces 4 again. The resulting spot-pattern in plane 5, which—as seen from the objective 70—is located in front of the disc 3, is relayed to the sample 73 via the tube-lens 13 and the objective 70, and creates a corresponding excitation pattern there, which rotates with the disc 3.

The mirrored surface 40 is interrupted by pinholes 8, which are located exactly on the optical axis of the micro-lenses 4 (in this case the mask is formed by the mirrored surface 40). In this manner the focal pattern and the pinhole pattern can be made confocal again by ensuring that the path length difference between excitation beam and emission is compensated for by means of a path length difference compensation arrangement 174. To this end the travel distance must correspond exactly to the optical distance 42 between the plane 5 of the focal pattern and the plane of the pinholes 8, so that the image plane 4 of the sample 73 (i.e., of the emission light pattern on the sample 73) coincides with the plane of the pinholes 8 like in the example of FIGS. 1 to 5.

Figure 7A:
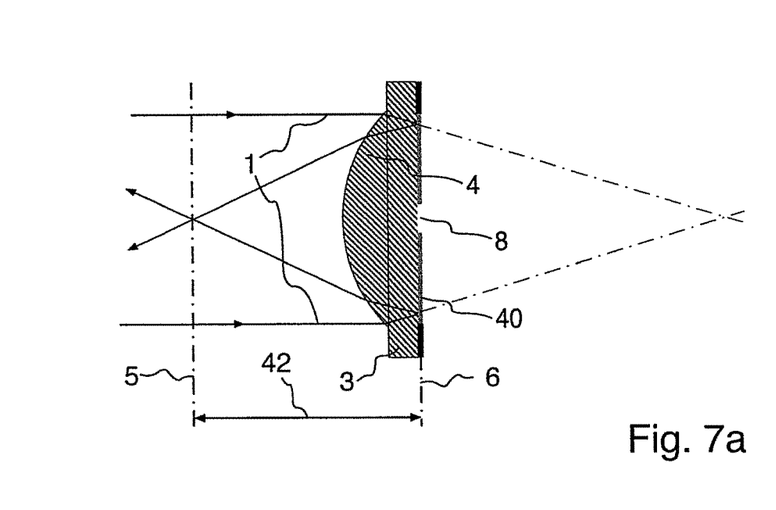
FIG. 7a is a schematic view of part of the system of FIG. 6 in the region of the Nipkow disc, wherein only the beam path of the illumination light is shown.
Figure 7B:
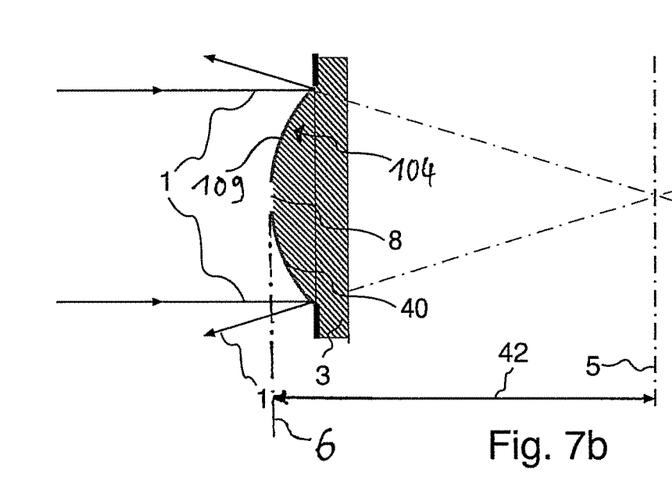
Figure 7C:
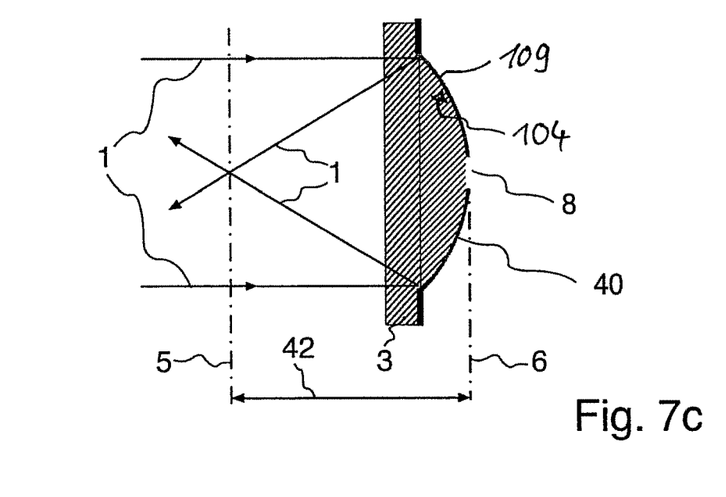
Figure 8:
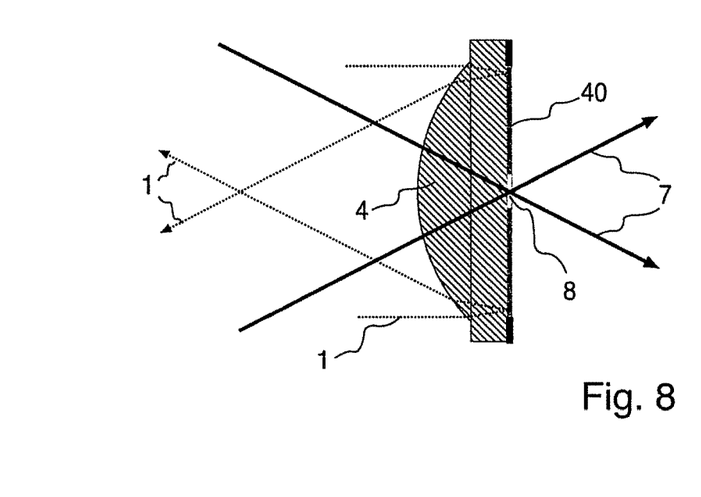
FIG. 8 is a view like FIG. 7a, wherein, however, in addition, the light collected from the sample is represented.

There are alternative embodiments, as is shown, for example, in FIGS. 7b & 7c, wherein the micro-lenses 4 of FIG. 7a are replaced by focusing micro-mirrors 104, having correspondingly curved mirror surfaces 109, which reflect the illumination light 1 in a manner so as to focus the illumination light 1 in the focal plane 5. The pinholes are realized by discontinuities 8 of these mirror surfaces 109. In the embodiment of FIG. 7b, the curvature of the mirror surfaces 109 is convex with regard to the direction of incidence of the illumination light 1, so that the focal plane 5 is located behind (with regard to the direction of incidence of the illumination light 1) the disc 3 (and thus at the side facing away from the sample 73). In the embodiment of FIG. 7c the curvature of the mirror surfaces 109, however, is concave with regard to the direction of incidence of the illumination light 1, so that the focal plane 5—like in the embodiment of FIG. 7a—is located in front of (with regard to the direction of incidence of the illumination light 1) the disc 3 (and thus at the side facing the sample 73).

In this regard the same applies as to the variants which are preferably used for multi-photon excitation: one will choose that embodiment which combines the most benefits with regard to its manufacturing.

Provided the path length difference compensation is adjusted correctly, the emitted light 7 passes through the pinholes 8 and can then be imaged, like in the example of FIG. 3, onto a camera (not shown) by using suitable optics.

Figures 9, 10:
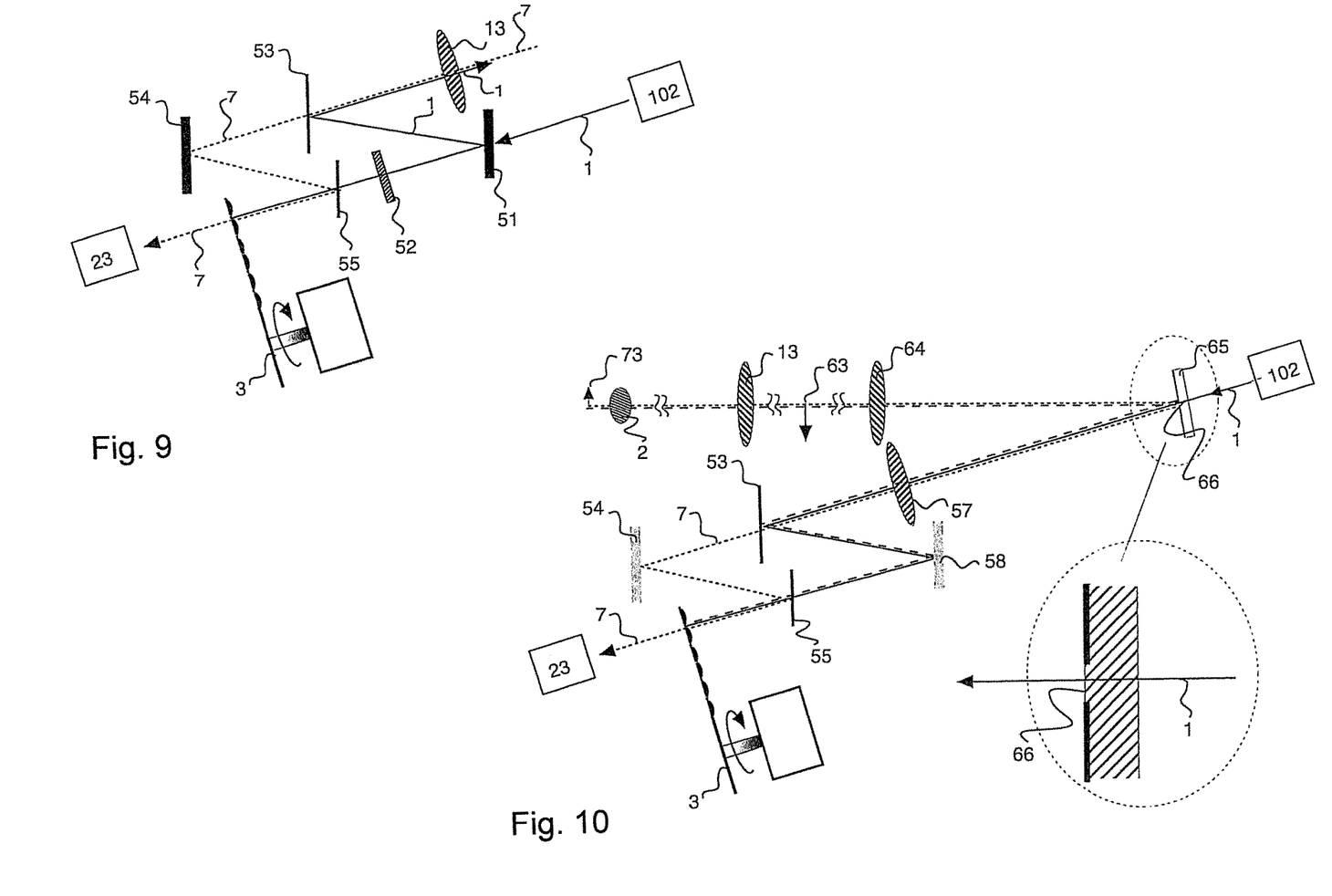
FIG. 9 is a schematic view of part of the system of FIG. 6, which includes a first example of a path length difference compensation arrangement and a first example of a coupling of the illumination light beam from the light source.
FIG. 10 is a view similar to FIG. 9, wherein an alternative example of a path length difference compensation arrangement and a coupling of the illumination light beam from the light source is shown.

In the one-photon variant, the path length difference compensation arrangement 174, which separates and combines again the excitation beams and emission beams, may also be used for coupling the illumination beam 1, originating from the light source 102, into the system. To this end a mirror 51 may be provided, as shown in FIG. 9, which transmits illumination beam 1, coming from the light source 102, so as to allow it reach the disc 3, but which, on the other hand, reflects the focal pattern generated by the micro-lenses 4 from the disc 3 so as to allow them to reach the sample 73. This is achieved by designing the mirror 51 as a polarizer, with in addition a λ/4 plate 52 being present on the way from the mirror 51 to the disc 3 in order to render the mirror 51 reflecting for the excitation light 1 coming from the disc 3, which excitation light previously already passed twice through the λ/4 plate 52.

In the example shown in FIG. 9 (wherein the path length difference compensation arrangement 174 is realized utilizing a combination of long-pass filter and short-pass filter) the emission light 7 first passes through the tube lens 13, then through a long pass filter 53, and is then reflected by a mirror 54 and thereafter by a short pass filter 55, prior to passing the pinholes 8 of the disc 3. The image of the disc 3 then is registered with the help of suitable optics on a camera chip (both of which are not shown). The excitation light 1, coming from the disc 3, passes through the short-pass filter 55, travels a second time through the λ/4 plate 52 and is reflected by the mirror 51 onto the long-pass filter 53, where it is reflected in order to be combined again with the beam path of the emission light 7. As in the example of FIG. 4, a variant comprising two long-pass filters is also possible to establish the desired path length difference compensation 174. It generally holds, also in this case, that the path length difference compensation arrangement may comprise as the first beam splitter—as seen from the objective—a long-pass, with the second beam splitter being also a long pass or a short-pass. Alternatively, the first beam splitter may be a short-pass, with the second beam splitter then being a long-pass or a short-pass filter.

The embodiment of FIG. 9 is relatively cumbersome for a practical realization due to the coupling by means of a polarizer mirror and the resulting need for use of a λ/4 plate.

A more elegant and therefore preferred variant, is shown in FIG. 10. It does not fall under the schematic representation of FIG. 6, instead it utilizes an additional relay lens system between sample 73 objective 70 and tube-lens 13 on one hand and Nipkow disc 3 with the micro-lens 4 on the other hand. The intermediate image 63, generated by the primary tube-lens 13, is imaged by means of a first (well corrected) lens 64 into infinity and is imaged by means of a second, likewise well corrected, lens 57 onto the disc 3. On its way to the disc the emission light 7 first passes through a long-pass filter 54 and then is reflected by a mirror 54 and a short-pass filter 55.

The mirror 65, which is located in the common focal plane of the lens 64 and the lens 57, has a small opening 66 in its center, through which the excitation light 1, coming from the light source 102, is focused and thereby is coupled into the beam-path illuminating the disk. The opening 66 is imaged (collimated) by the lens 57 into infinity, it is reflected by the long-pass filter 53 and the mirror 58, and it reaches, after having passed the short-pass 55, the disc 3, where the micro-optics located there, comprising the micro-lenses 4 and the mask reflects the beam 1, reflects, by means of the mirrored surface 40, the beam 1 back and thereby generates the desired spot pattern in the plane 7. The spot pattern then travels backwards along the described beam path, but—due to the much higher NA (numerical aperture) of the spot pattern compared to the NA of the collimated beam 1—the excitation beam on its way to the sample occupies a much larger area on the mirror 65, so that the opening 66 located there only "eats up" only a negligible portion of the illumination light 1. From the mirror 65 on, the excitation light beam 1 takes the same path as the emission light beam 7, but in opposite direction.

It is self-evident that also in this embodiment the travel distance differences of excitation light beam and emission light beam have to be exactly adjusted to each other in order to achieve the desired confocal effect. However, since excitation beam and emission beam not only have to be most exactly adjusted to each other with regard to the travel distances but also with regard to the position of the emission focal points relative to the pinholes 8, it is advisable to recalibrate the system after each filter change and to re-adjust, if necessary, the system by (motor-driven) adjustment of one of the mirrors 54 and 58, respectively. To this end, a thin fluorescent layer, with suitable excitation and emission spectrum may be introduced into the intermediate image plane 63, and mirror 54 or 58 may adjusting along two axes until a maximal signal is seen on the camera.

The present invention is preferably used for fluorescence microscopy with one-photon excitation, or multi-photon excitation (mainly two photon excitations), so that the illumination light is excitation light and the light collected from the sample is fluorescence emission light; in one-photon excitation the emission light is of longer wavelength than the excitation light, and in multi-photon excitation the emission light is of shorter wavelength than the excitation light.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A system for confocal observation of a sample, comprising:
    a mask which is arranged in both an illumination beam path and in an image beam path and which is rotatable around a central axis, the mask comprising openings arranged in a geometric arrangement in a pinhole plane,
    an arrangement of focusing micro-optics aligned with the geometric arrangement of the openings of the mask so as to focus the illumination light by each of the micro-optics in a focal plane in order to generate a focal pattern there, and
    an optical assembly comprising an objective configured to image the focal pattern onto the sample for generating an illumination pattern moving across the sample and to collect light from the sample by the objective and to image it onto the openings of the mask for confocal filtering,
    wherein the focal plane and the pinhole plane are separated by a distance from each other,
    wherein the optical assembly comprises a path length difference compensation arrangement which is selective with regard to the illumination light and the light collected from the sample so as to compensate for the path length difference between the location of the focal plane of the micro-lenses and the location of the pinhole plane for the light collected from the sample, and
    wherein the optical assembly comprises a tubular lens cooperating with the objective, and wherein the path length difference compensation arrangement is located in the beam path between the tubular lens and the mask.

2. The system of claim 1, wherein the focal plane is located on a side of the mask facing the sample in a direction along the beam path.

3. The system of claim 1, wherein an imaging optics is provided for imaging the light collected from the sample and filtered through the openings of the mask onto a detector by imaging the pinhole plane onto the detector.

4. The system of claim 1, wherein the openings of the mask and the micro-optics are fixed with regard to each other.

5. The system of claim 4, wherein each opening is located on the optical axis of one of the micro-optics.

6. The system of claim 5, wherein the mask and the micro-optics are arranged on a common disc.

7. The system of claim 1, wherein the openings of the mask and the micro-optics, respectively, are arranged concentrically around the central axis.

8. The system of claim 1, wherein the mask is configured as a Nipkow disc.

9. The system of claim 1, wherein the micro-optics comprise micro-lenses or focusing micro-mirrors.

10. The system of claim 1, wherein the path length difference compensation arrangement comprises a first dichroic beam splitter for splitting the beam paths of the illumination light and the light collected from the sample, and a second dichroic beam splitter for recombining the beam paths of the illumination light and the light collected from the sample and is configured to guide the light collected from the sample and the illumination light along paths between the first dichroic beam splitter and the second dichroic beam splitter, which have different lengths, and wherein the difference in length corresponds to the path length difference between the position of the focal plane and the position of the pinhole plane.

11. The system of claim 10, wherein the path length difference compensation arrangement comprises a first reflecting element for the light collected from the sample and a second reflecting element for the illumination light.

12. The system of claim 11, wherein the reflecting elements directs the light, having passed through the first dichroic beam splitter to a first side of the second dichroic beam splitter, and wherein the other one of the reflecting elements directs the light, reflected by the first dichroic beam splitter, to the other side of the second dichroic beam splitter.

13. The system of claim 10, wherein one of the dichroic beam splitters of the path length difference compensation arrangement is designed as a long-pass, and wherein the other one of the dichroic beam splitters of the path length difference compensation arrangement is designed as a long-pass or as a short-pass.

14. The system of claim 1, wherein the system is designed for fluorescence excitation of the sample in order to collect fluorescence emission light from the sample.

15. The system of claim 1, wherein a partial illumination arrangement is provided in the beam path between the illumination light source and the micro-optics for illuminating at a time only part of the micro-optics with illumination light.

16. The system of claim 15, wherein the partial illumination arrangement is a scanning arrangement for moving the illumination light continuously across the micro-optics.

17. The system of claim 16, wherein the system is configured to control a detector for the light collected from the sample in a rolling-shutter mode, so that a rolling shutter moves across the sample according to the motion of the illumination light.

18. The system of claim 16, wherein the partial illumination arrangement comprises a galvanometer mirror.

19. A system for confocal observation of a sample, comprising:
a mask which is arranged in both an illumination beam path and in an image beam path and which is rotatable around a central axis, the mask comprising openings arranged in a geometric arrangement in a pinhole plane,
an arrangement of focusing micro-optics aligned with the geometric arrangement of the openings of the mask so as to focus the illumination light by each of the micro-optics in a focal plane in order to generate a focal pattern there, and
an optical assembly comprising an objective configured to image the focal pattern onto the sample for generating an illumination pattern moving across the sample and to collect light from the sample by the objective and to image it onto the openings of the mask for confocal filtering,
wherein the focal plane and the pinhole plane are separated by a distance from each other,
wherein the optical assembly comprises a path length difference compensation arrangement which is selective with regard to the illumination light and the light collected from the sample so as to compensate for the path length difference between the location of the focal plane of the micro-lenses and the location of the pinhole plane for the light collected from the sample, and
wherein the mask is transmitting for the illumination light and is non-transmitting for the light collected from the sample.

20. The system of claim 19, wherein a short-pulse light source is provided for emitting light as illumination light for multi-photon excitation, and wherein the mask is designed as a long-pass filter.

21. The system of claim 19, wherein the micro-optics are located at the side of the mask facing the sample in a direction along the beam path.

22. The system of claim 19, wherein a beam splitter is provided for separating light from the sample from illumination light.

23. The system of claim 22, wherein the beam splitter is transmitting for the illumination light and is reflecting for light collected from the sample.

24. The system of claim 23, wherein the beam splitter is arranged in the beam path between a light source for the illumination light and the mask.

25. The system of claim 19, wherein the micro-optics are micro-lenses, and wherein the mask and the micro-lenses are arranged on opposite sides of a disc.

26. The system of claim 19, wherein the micro-optics are micro-lenses, and wherein the mask is provided as a coating on the micro-lenses, the coating being provided with the openings and being non-transmitting for light collected from the sample.

27. A system for confocal observation of a sample, comprising:
a mask which is arranged in both an illumination beam path and in an image beam path and which is rotatable around a central axis, the mask comprising openings arranged in a geometric arrangement in a pinhole plane,
an arrangement of focusing micro-optics aligned with the geometric arrangement of the openings of the mask so as to focus the illumination light by each of the micro-optics in a focal plane in order to generate a focal pattern there, and
an optical assembly comprising an objective configured to image the focal pattern onto the sample for generating an illumination pattern moving across the sample and to collect light from the sample by the objective and to image it onto the openings of the mask for confocal filtering,
wherein the focal plane and the pinhole plane are separated by a distance from each other,
wherein the optical assembly comprises a path length difference compensation arrangement which is selective with regard to the illumination light and the light collected from the sample so as to compensate for the path length difference between the location of the focal plane of the micro-lenses and the location of the pinhole plane for the light collected from the sample, and
wherein the micro-optics are located as micro-lenses on a side of the mask which faces the sample with regard to the beam path, wherein the mask is reflecting for the illumination light, and wherein the arrangement is configured to direct the illumination light from the side facing the sample with regard to the beam path to the micro-optics so that the illumination light passes twice through the micro-optics in order to generate the focal pattern.

28. The system of claim 1, wherein the micro-optics are focusing micro-mirrors having curved mirror surfaces which reflect the illumination light, wherein the openings of the mask are realized as openings in the mirror surfaces, and wherein the mirror surfaces are non-transmitting for the light collected from the sample.

29. The system of claim 27, wherein an optical coupling element is provided which is transmissive for an illumination light beam emitted by an illumination light source for directing the illumination light beam onto the micro-optics and the mask (40), and wherein the optical coupling element is mainly reflecting for illumination light reflected by the mask for directing the illumination light reflected by the mask towards the sample.

30. The system of claim 29, wherein the illumination light beam emitted by the illumination light source is directed anti-parallel with regard the illumination light reflected by the mask onto the micro-optics and the mask.

31. The system of claim 29, wherein the coupling element is a polarizer, and wherein a λ/4 plate is arranged in the beam path between the polarizer and the mask so as to rotate the polarization of the illumination light reflected by the mask, so that this light is reflected by the polarizer.

32. The system of claim 31, wherein the polarizer is one of the reflecting elements of the path length difference compensation arrangement.

33. The system of claim 29, wherein the coupling element is arranged in the beam path between the objective and the path length difference compensation arrangement.

34. The system of claim 33, wherein the coupling element is a mirror for the illumination light reflected by the mask, which mirror is arranged in an infinite space created by a relay arrangement and comprises an opening for allowing the illumination light beam emitted by the illumination light source to pass anti-parallel with regard to the illumination light reflected by the mask.

35. The system of claim 34, wherein the relay arrangement comprises a first lens and a second lens, wherein the mirror is arranged in the beam path between the two lenses, and wherein the first lens images an intermediate image created by the tubular lens into infinity, and wherein the second lens is constructed so as to image the intermediate image generated by the tubular lens onto the pinhole plane.

36. The system of claim 35, wherein the second lens is constructed so as to image the opening of the mirror into infinity.

* * * * *